US011737959B2

(12) United States Patent
Heilmann et al.

(10) Patent No.: US 11,737,959 B2
(45) Date of Patent: Aug. 29, 2023

(54) TWO-PART OXIDATIVE DYEING COMPOSITION

(71) Applicant: Kao Corporation, Tokyo (JP)

(72) Inventors: Jens Heilmann, Darmstadt (DE); Diana Bauer, Darmstadt (DE); Steven Breakspear, Darmstadt (DE); Peter Bauer, Darmstadt (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 17/773,455

(22) PCT Filed: Oct. 30, 2020

(86) PCT No.: PCT/EP2020/080539
§ 371 (c)(1),
(2) Date: Apr. 29, 2022

(87) PCT Pub. No.: WO2021/084085
PCT Pub. Date: May 6, 2021

(65) Prior Publication Data
US 2022/0401319 A1 Dec. 22, 2022

(30) Foreign Application Priority Data
Oct. 31, 2019 (EP) ..................................... 19206514

(51) Int. Cl.
*A61Q 5/10* (2006.01)
*A61K 8/22* (2006.01)
*A61K 8/06* (2006.01)
*A61K 8/34* (2006.01)
*A61K 8/40* (2006.01)
*A61K 8/49* (2006.01)
*A61Q 5/08* (2006.01)

(52) U.S. Cl.
CPC ................ *A61K 8/22* (2013.01); *A61K 8/062* (2013.01); *A61K 8/34* (2013.01); *A61K 8/40* (2013.01); *A61K 8/4953* (2013.01); *A61Q 5/08* (2013.01); *A61Q 5/10* (2013.01); *A61K 2800/4322* (2013.01); *A61K 2800/48* (2013.01); *A61K 2800/596* (2013.01)

(58) Field of Classification Search
CPC . A61K 8/22; A61K 8/062; A61K 8/34; A61K 8/40; A61K 8/4953; A61K 2800/4322; A61K 2800/48; A61Q 5/08; A61Q 5/10
USPC .............................................................. 8/405
See application file for complete search history.

(56) References Cited

U.S. PATENT DOCUMENTS

| 2002/0157191 A1* | 10/2002 | Casperson ........... A61K 8/8164 8/408 |
| 2002/0194683 A1* | 12/2002 | Casperson ............. A61K 8/416 8/408 |
| 2005/0283925 A1* | 12/2005 | Glenn ...................... A61Q 5/10 8/405 |
| 2010/0158844 A1 | 6/2010 | Braida-Valerio et al. |

FOREIGN PATENT DOCUMENTS

| DE | 10 2006 061 830 A1 | 6/2008 |
| DE | 10 2007 041 493 A1 | 3/2009 |
| EP | 2 198 923 A2 | 6/2010 |
| EP | 2 559 456 A2 | 2/2013 |
| WO | WO 2009/053180 A1 | 4/2009 |

OTHER PUBLICATIONS

STIC Search Report dated Apr. 6, 2023.*
International Search Report and Written Opinion dated Feb. 8, 2021 in PCT/EP2020/080539, filed on Oct. 30, 2020, citing documents AO-AR therein, 4 pages.
Extended European Search Report dated Apr. 8, 2020 in European Application 19206514.2, filed on Oct. 31, 2019, citing documents AO-AR therein, 5 pages.
MINTEL #6713099, 2019, http://www.gnpd.com, 2 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A two-part oxidative dyeing composition is described. The two-part composition has an alkaline first part comprising oxidative dye couplers and/or oxidative dye precursors, and a second part comprising hydrogen peroxide, xanthine and/or its derivatives, and a lipophilic compound. The second part is formulated as water-in-oil emulsion and it was unexpectedly found that xanthines stabilize the viscosity of the second part composition allowing for improved dyeing performance.

16 Claims, No Drawings

TWO-PART OXIDATIVE DYEING COMPOSITION

CROSS-REFERENCE TO RELATED APPLICATIONS

The present application is a 35 U.S.C. § 371 national stage application of International patent application PCT/EP2020/080539, filed Oct. 30, 2020, which is based on and claims the benefit of priority to European Application No. 19206514.2, filed Oct. 31, 2019. The entire contents of these applications are incorporated herein by reference.

FIELD OF THE INVENTION

The present invention is directed to a two-part oxidative dyeing composition, a method for oxidative dyeing of keratin fibers, and a kit-of-parts for oxidative dyeing.

BACKGROUND OF THE INVENTION

Aqueous hydrogen peroxide-containing compositions are an essential component for effectively dyeing keratin fibers. In particular cosmetic industry relies on the performance of these compositions. Typically, hydrogen-peroxide compositions are formulated as emulsions.

However, a common problem of such emulsion compositions is that storage stability especially under suboptimal temperature conditions is dissatisfactory. For example, consumers living in countries closer to the equatorial line can very often not guarantee proper storage of the compositions at room temperature. As a result, the user is confronted with lower performance of dyeing processes compared to results obtained a couple of months ago with the same composition.

However, it is essential for the user of hydrogen-peroxide emulsion compositions that they have a long shelf life in order to retain their original performance.

The prior art has not sufficiently solved this problem.

For example, EP2198923 focuses on emulsion stability by selecting certain surfactants and concentration ranges for improving stability.

Xanthine and its derivatives are well-known ingredients in pharmaceutical and food industry. Moreover, cleansing compositions comprising caffeine are well-known (e.g. Mintel #6713099).

WO2009/053180 discloses aqueous oxidizing compositions comprising 5% by weight or less of hydrogen peroxide and purine derivatives, in particular caffeine. It was found that purine derivatives reduce damage to keratin fibers.

SUMMARY OF THE INVENTION

Thus, the first object of the present invention is a two-part oxidative dyeing composition comprising:
 a dyeing composition A having a pH in the range of 7 to 12 and comprising one or more oxidative dye precursor(s) and/or oxidative dye couplers, and one or more alkalizing agent(s),
 an aqueous oxidizing composition B having a pH in the range of 1 to 6 comprising:
 a) hydrogen peroxide, and
 b) one or more compound(s) according to the following structure:

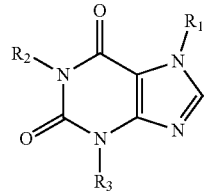

wherein $R_1$, $R_2$, and $R_3$ are independently selected from H and $CH_3$, and/or their mixtures, and
 c) one or more lipophilic compound,
 wherein composition B is an oil-in-water emulsion.

The second object of the present invention is a method for oxidative dyeing of keratin fibers, preferably human keratin fibers, more preferably human hair comprising the steps of:
 i) providing the two-part composition as defined above and mixing the compositions to provide a ready-to-use composition having a pH in the range of 7 to 12,
 ii) applying the ready-to-use composition onto keratin fibers and leaving it for a time period in the range of 1 to 60 min,
 iii) rinsing off the keratin fibers and optionally shampooing the keratin fibers.

A third object of the present invention is a kit-of-parts comprising the two-part composition as defined above and one more composition selection from:
 a bleach powder composition comprising one or more persalt(s) and/or peroxy salt(s) and one or more alkalizing agent(s),
 an aqueous bleaching composition comprising one or more alkalizing agent(s) and having a pH in the range of 7 to 12.

DETAILED DESCRIPTION OF THE INVENTION

Despite the attempts of the prior art, no satisfactory solution could be delivered to maintain performance and storage stability of hydrogen peroxide emulsion compositions, in particular their physical storage stability.

Inventors of the present invention have unexpectedly found out that xanthine derivatives increase storage stability of hydrogen peroxide compositions at room, lowered, and elevated temperature. Moreover, xanthine derivatives enable the maintenance of composition viscosity over storage. This ensures mixability of the two-part composition independently of their prior storage history and avoids handling problems for customers. Moreover, oxidative dyeing processes were found to be more consistent in performance over time by the inventive principle.

Oxidative Dyeing Composition A

The oxidative dyeing composition A has a pH in the range of 7 to 12 and comprises one or more oxidative dye precursor(s) and/or oxidative dye couplers, and one or more alkalizing agent(s).

It is preferred from the viewpoint of dyeing performance that the pH of the oxidative dyeing composition A preferably is 7.5 or more, more preferably 8.0 or more, further more preferably 8.5 or more.

It is preferred from the viewpoint of cosmetic safety and dyeing performance that the pH of the dyeing composition A preferably is 11 or less, more preferably 10.5 or less, further more preferably 10.0 or less.

For attaining the above-mentioned effects, it is preferred that the pH of the of the oxidative dyeing composition A is in the range of 7.5 to 11, more preferably 8.0 to 10.5, furthermore preferably 8.5 to 10.0.

The oxidative dying composition A comprises one or more oxidative dye precursors and/or oxidative dye couplers.

Suitable oxidative dye precursors are, for example, p-phenylendiamine and/or its derivatives, p-aminophenol and/or its derivatives, and heterocyclic compounds such as diaminopyrazols and substituted pyrimidines and/or their derivatives.

Example oxidative dye precursors are p-phenylenediamine, p-aminophenol, 2,5-diamino-toluene, 2-n-propyl or 2-ethyl-p-phenylenediamine, 2,6-di-methyl-p-phenylenediamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethylamino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methyl pyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene, 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof, and/or their mixtures.

Suitable oxidative dye couplers are resorcinol and/or its derivatives, m-aminophenol and/or its derivatives, m-phenylenediamine and/or its derivatives, pyridines and/or its derivatives, and naphthole and/or its derivatives.

Examples for oxidative dye couplers are 5-amino-2-methylphenol, 2-methyl-5-hydroxyethylaminophenol, 2,4,-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hydroxy-ethyl) amino] benzene, α-naphthol, 4,6-dichlororesorcinol, 1,3-diaminotoluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)-benzene or the water-soluble salts thereof, and mixture thereof.

The suitable total concentration of oxidative dye precursors and/or oxidative dye couplers is in the range of 0.001% to 5% by weight, preferably 0.01% to 4% by weight, more preferably 0.05% to 3% by weight, still more preferably 0.1% to 2% by weight, calculated to the total weight of the oxidative dyeing composition A.

The oxidative dyeing composition A comprises one or more alkalizing agent. Preferably, one or more alkalizing agent(s) is selected from ammonia, alkyl- or alkanolamines according to the general structure

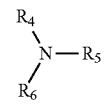

wherein $R_4$, $R_5$, and $R_6$ are same or different from H, preferably selected from $C_1$ to $C_4$-alkyl, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_4$, $R_5$, or $R_6$ is different from H, from the viewpoint of cosmetic safety and dyeing performance.

It is preferred from the viewpoint of dyeing intensity that the alkalizing agent is selected from ammonia and/or its salts, monoethanolamine and/or its salts, and/or 2-aminomethyl propanol, and/or their mixtures.

It is further preferred from the viewpoint of sufficient alkalinity and dyeing intensity that the concentration of alkalizing agents in the oxidative dyeing composition A before mixing is in the range of 0.25% to 15%, more preferably 0.5% to 12.5%, still more preferably 0.75% to 10%, and still more preferably 1% to 7.5% by weight, calculated to the total weight of the oxidative dyeing composition A before mixing.

The oxidative dyeing composition may be in the form of a thickened gel, an emulsion, or a thickened emulsion.

For forming an emulsion, the oxidative dyeing composition A may comprise one or more lipophilic compound according to c), as disclosed in detail for the aqueous oxidative composition B.

For forming a thickened gel and/or a thickened emulsion, the oxidative dyeing composition A may further comprise a thickening polymer, as disclosed for the aqueous oxidative composition B.

Furthermore, from the viewpoint of wettability and formulation stability, the oxidative dyeing composition A may further comprise one or more surfactant(s) as compound according to d), as disclosed for the aqueous oxidizing composition B.

Aqueous Oxidizing Composition B

The aqueous oxidizing composition B has a pH in the range of 1 to 6 and comprises:

a) hydrogen peroxide, and b) one or more compound(s) according to the following structure:

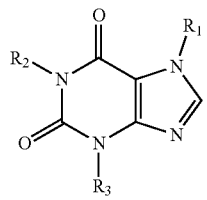

wherein $R_1$, $R_2$, and $R_3$ are independently selected from H and $CH_3$, and/or their mixtures, and c) one or more lipophilic compound, wherein composition B is an oil-in-water emulsion.

It is preferred from the viewpoint of storage stability and safety of the composition that the pH of is 1.25 or more, more preferably 1.5 or more, further more preferably 2 or more.

It is preferred from the viewpoint of storage stability of the composition that the pH of the composition is 5 or less, more preferably 4 or less, further more preferably 3 or less.

For attaining the above-mentioned effects, it is preferred that the pH of the composition is in the range of 1.25 to 5, more preferably in the range of 1.5 to 4, further more preferably in the range of 2 to 3.

It is further preferred from the viewpoint of product performance that the concentration of the compound according to a) is in the range of more than 1% by weight or more, more preferably 2% by weight or more, further more preferably 3% by weight or more, calculated to the total weight of the composition.

It is further preferred from the viewpoint of product performance and user safety that the concentration of the compound according to a) is 20% by weight or less, more preferably 15% by weight or less, further more preferably 12% by weight or less, calculated to the total weight of the composition.

For attaining the above-mentioned effects, it is preferred that the concentration of the compound according to a) is in the range of more than 1% to 20% by weight, more preferably 2% to 15% by weight, further more preferably 3% to 12% by weight, calculated to the total weight of the composition.

Suitable xanthine and/or xanthine derivatives according to compound b) are

Xanthine with $R_1=R_2=R_3=H$,
Theobromine with $R_1=R_3=CH_3$ and $R_2=H$,
Theophylline with $R_2=R_3=CH_3$ and $R_1=H$, and
Caffeine with $R_1=R_2=R_3=CH_3$.

Mixtures of the above are suitable as well.

It is preferred from economic viewpoint that at least one compound according to b) is caffeine.

It is further preferred from the viewpoint of stabilizing performance that the total concentration of compounds according to b) is 0.001% by weight or more, more preferably 0.01% by weight or more, further more preferably 0.02% by weight or more, still more preferably 0.03% by weight or more, calculated to the total weight of the composition B.

It is further preferred from the viewpoint of economic reasons as well as stabilizing performance that the total concentration of compounds according to b) is 0.5% by weight or less, more preferably 0.25% by weight or less, further more preferably 0.1% by weight or less, still more preferably 0.08% by weight or less, calculated to the total weight of the composition B.

For attaining the above-mentioned effects it is preferred that the total concentration of compounds according to b) is in the range of 0.001% to 0.5% by weight, preferably 0.01% to 0.25% by weight, more preferably 0.02% to 0.1% by weight, still more preferably 0.03% to 0.08% by weight, calculated to the total weight of the composition B.

The aqueous oxidizing composition B is an oil-in-water emulsion and comprises one or more lipophilic compound(s) as compound(s) according to c).

Preferably, compounds according to c) are selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and hydrocarbon-based products, and/or their mixtures, from the viewpoint of cosmetic compatibility.

Suitable $C_{12}$ to $C_{22}$ fatty alcohols are are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

Suitable hydrocarbon-based products are mineral oil, paraffins, and Vaseline.

It is preferred from the viewpoint of forming a stable composition and user friendliness that the total concentration of compounds according to c) is 1% by weight or more, more preferably 2% by weight or more, further more preferably 3% by weight or more, calculated to the total weight of the composition.

It is preferred from the viewpoint of forming a stable composition that the total concentration of compounds according to c) is 20% by weight or less, more preferably 15% by weight or less, further more preferably 12% by weight or less, calculated to the total weight of the composition.

For attaining the above-mentioned effects, the total concentration of compounds according to c) is in the range of 1% to 20% by weight, preferably 2% to 15% by weight, more preferably 3% to 12% by weight, calculated to the total weight of the composition.

Surfactants as Compounds According to d)

The oxidative dyeing composition A and/or the aqueous oxidizing composition B of the present invention may further comprise one or more surfactant(s) as compound(s) according to d), preferably selected from non-ionic surfactants, anionic surfactants, cationic surfactants, and/or amphoteric/zwitterionic surfactants, and/or their mixtures, more preferably selected from anionic surfactants and/or non-ionic surfactants, from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures.

Suitable examples are alkyl sulfate or preferably ethoxylated alkyl ether sulfate surfactant or mixtures thereof having an alkyl chain length of $C_{10}$ to $C_{22}$.

Suitable non-ionic surfactants may be selected from alkyl glycosides, alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants. Suitable examples are cetrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of each of the compositions A and/or B, from the viewpoint of enhancing wettability of keratin fibers and mixability with other compositions, in particular with the oxidative dyeing composition A.

Viscosity of Aqueous Oxidizing Composition B

The viscosity of the aqueous oxidizing composition B may be adjusted by emulsion components to achieve a cosmetically safe viscosity.

It is preferred from the viewpoint of cosmetic safety and mixability that the aqueous oxidizing composition B composition of the present invention has viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions. A suitable viscometer is a Brookfield viscometer with spindle #4.

Thickening Polymers

In case the viscosity needs to be further adjusted, the oxidative dyeing composition A and/or the aqueous oxidizing composition B may comprise one or more thickening polymers, from the viewpoint of cosmetic safety.

The composition of the present invention comprises one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 1 and 6 having a viscosity of at least 1,000 mPas measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as ($C_2$-$C_8$)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers of the present invention are 0.1% by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers of the present invention are 15% by weight or less, more preferably 12% by weight or more, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers in the composition of the present invention is in the range of 0.1% to 15% by weight, preferably 0.25% to 12% by weight, more preferably in the range of 0.5% to 10% by weight, calculated to the total weight of the composition.

Ready-to-Use Mixture and Method for Oxidative Dyeing

The present invention is also directed to a method for oxidative dyeing of keratin fibers, preferably human keratin fibers, more preferably human hair comprising the steps of:

i) providing the two-part composition as defined above and mixing the compositions to provide a ready-to-use composition having a pH in the range of 7 to 12, ii) applying the ready-to-use composition onto keratin fibers and leaving it for a time period in the range of 1 to 60 min, iii) rinsing off the keratin fibers and optionally shampooing the keratin fibers.

The oxidative dyeing composition A is mixed with the aqueous oxidizing composition B to form a ready-to-use composition. Suitable mixing ratios by weight are 5:1 to 1:5 (oxidative dyeing composition A:aqueous oxidizing composition B). Customarily, suitable mixing ratios are 1:1, 1:2, and 1:3 by weight (oxidative dyeing composition A:aqueous oxidizing composition B).

Suitably, the pH of the ready-to-use composition is in the range of 7 to 12. It is preferred from the viewpoint of accelerated dyeing that the pH of the ready-to-use composition is in the range of 7.5 to 11, more preferably 8.0 to 10.5.

The ready-to-use composition is then applied to keratin fibers and left for a time period of 1 min to 60 min as defined in step ii). Preferred time ranges for step ii) are 5 min to 45 min, more preferred ranges are 10 min to 35 min, from the viewpoint of sufficiently dyeing the keratin fibers.

During step ii) and after applying the ready-to-use composition, heat may be applied from the viewpoint of accelerating oxidative dyeing. Suitable temperature ranges are 30° C. to 50° C., from the viewpoint of oxidative dyeing speed and cosmetic safety.

After that, the ready-to-use composition is rinsed-off from keratin fibers and optionally they are shampooed and optionally blow-dried.

Kit-of-Parts

Kit-of-parts comprising the two-part composition as defined above and one more composition selected from:

a bleach powder composition comprising one or more persalt(s) and/or peroxy salt(s) and one or more alkalizing agent(s), an aqueous bleaching composition comprising one or more alkalizing agent(s) and having a pH in the range of 7 to 12.

The bleach powder composition comprises one or more persalt(s) and/or peroxy salt(s). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium and ammonium persulfate.

It is preferred from the viewpoint of bleaching power and cosmetic safety that the total concentration of persalts and/or peroxy salts in the bleach powder composition is in the range of 10% to 80% by weight, preferably in the range of 15% to 70% by weight, more preferably in the range of 20% to 60% by weight, and still more preferably in the range of 25% to 60% by weight, calculated to the total weight of the bleach powder composition.

The bleach powder composition further comprises one or more alkalizing agent(s). Suitable alkalizing agent(s) are metasilicates, in particular sodium metasilicate. It is preferred from the viewpoint of alkalinity that the concentration of metasilicates in the bleach powder composition is in the range of 1% to 20% by weight, more preferably 5% to 15% by weight, calculated to the total weight of the bleach powder composition.

Other suitable alkalizing agent(s) are carbonate and bicarbonate alkali salts such as sodium, potassium, and ammonium salts. The preferred salts are bicarbonate salts and especially preferred is ammonium bicarbonate, from the viewpoint of buffer capacity. Suitable concentration of carbonates in the bleach powder composition is in the range of 0.25% to 10% by weight, preferably in the range of 0.5% to 7.5% by weight, more preferably in the range of 0.75% to 5% by weight, and still more preferably in the range of 1% to 4% by weight, calculated to the total weight of the bleach powder composition, from the viewpoint of buffer capacity and low hair damage.

The bleach powder composition is then mixed with the aqueous oxidizing composition B of the present invention to form a ready-to-use composition. Suitable mixing ratios by weight are 5:1 to 1:5 (bleach powder:inventive composition B). Customarily, suitable mixing ratios are 1:1, 1:2, and 1:3 by weight (bleach powder:inventive composition B).

Suitably, the pH of the ready-to-use composition is in the range of 7 to 12. It is preferred from the viewpoint of accelerated dyeing that the pH of the ready-to-use composition is in the range of 7.5 to 11, more preferably 8.0 to 10.5.

The ready-to-use composition is then applied to keratin fibers and left for a time period of 1 min to 60 min. Preferred time ranges for bleaching are 5 min to 45 min, more preferred ranges are 10 min to 35 min, from the viewpoint of sufficiently bleaching keratin fibers.

Optionally, heat may be applied while leaving the ready-to-use composition onto keratin fibers. Suitable temperature ranges are 30° C. to 50° C.

After that, the ready-to-use composition is rinsed-off from keratin fibers and optionally they are shampooed and optionally blow-dried. Then the oxidative dyeing method is applied as defined above. The aqueous lightening composition of step xii) before mixing preferably is an emulsion comprising one or more lipophilic compound, as also disclosed for the inventive composition.

Alternatively, an aqueous lightening composition is used for lightening/bleaching of keratin fibers. This composition preferably has a pH in the range of 8 to 11, more preferably in the range of 8.5 to 10.5, from the viewpoint of lightening performance.

Suitable mixing ratios are similar to the ones disclosed for the bleaching process above while using an aqueous composition instead of a bleaching powder.

Such kits as disclosed above are advantageous as three-part bleaching/dyeing compositions.

The following examples are to illustrate the present invention, but not to limit it.

EXAMPLES

Example 1

The following oxidative dyeing composition A was prepared:

|  | % by weight |
| --- | --- |
| Cetearyl alcohol | 12 |
| Sodium cetearyl sulfate | 2 |
| Cocamide MEA | 5 |
| Oleic acid | 2 |
| Tetrasodium EDTA | 1 |
| Sodium sulfite | 1 |
| Ammonium hydroxide | 5 |
| Ammonium chloride | 1 |
| Toluene-2,5-Diamine sulfate | 0.75 |
| Resorcinol | 0.10 |
| 4-Chlorresorcinol | 0.25 |
| m-Aminophenol | 0.05 |
| 4-Amino-2-Hydroxytoluene | 0.05 |
| Fragrance | 0.5 |
| Water | ad 100 |

The above composition had a pH of 9.9.

The following aqueous oxidizing compositions B were prepared by dispersing cetearyl alcohol and sodium lauryl sulfate in water and heating the mixture under constant stirring to 60° C. After cooling, the mixture is then added to hydrogen peroxide solution under constant stirring. Then caffeine was dissolved as compound according to b):

| Ingredient | Inventive composition 1 [% by weight] | Comparative composition 1 [% by weight] |
| --- | --- | --- |
| Caffeine | 0.03 | — |
| Hydrogen peroxide | | 9.0 |
| Cetearyl alcohol | | 4.0 |
| Sodium lauryl sulfate | | 0.5 |
| Phosphoric acid | | q.s. ad pH 2.0 |
| Water | | Ad 100.0 |

The compositions were prepared and stored under controlled conditions at 40° C. for 1 month. Viscosity was measured and the results were found as follows:

|  | Inventive composition 1 [mPas] | | | | Comparative composition 1 [mPas] | | | |
| --- | --- | --- | --- | --- | --- | --- | --- | --- |
| Time | Storage Temperature | | | | | | | |
| [months] | 5° C. | 25° C. | 40° C. | 50° C. | 5° C. | 25° C. | 40° C. | 50° C. |
| 0 | | 7,360 | | | | 8,360 | | |
| 1 | 12,800 | 11,400 | 13,920 | 14,080 | 45,000 | 14,400 | 50,600 | 49,400 |

A further visual inspection of the compositions was performed and it was confirmed by the human operator that comparative composition 1 was foamy and presented gas bubbles at the surface, whereas inventive composition 1 did neither present any bubbles nor was it foamy.

As a result of the viscosity test, the viscosity of the inventive composition 1 increased by about 50% over 1 month, whereas the viscosity of the comparative composition 1 increased over 500-600% under certain storage conditions.

The oxidative dyeing composition A from above was then mixed with the inventive composition 1 and comparative composition 1 both stored after 1 month at 40° C. at a weight ratio of 1:2 (oxidative dyeing composition A:inventive composition 1) to yield a ready-to-use composition having a pH around 9.5.

Due to the high viscosity of comparative composition 1, proper mixing with the oxidative dyeing composition was not possible leaving visible inhomogeneity in the ready-to-use mixture. For complete dissolution, the mixture had to be further diluted with composition B.

The ready-to-use compositions were then applied onto human hair and left for 30 min at 40° C. After that, the compositions were rinsed-off with water, the hair was shampooed, and blow-dried.

The hair was found to be intensely colored red-brown with inventive composition 1, whereas the color intensity and brilliance was visually much lower for the hair streak dyed with comparative composition 1.

Example 2

Composition B

|  | % by weight |
| --- | --- |
| Caffeine | 0.01 |
| Cetearyl alcohol | 4.0 |
| Sodium lauryl sulfate | 0.8 |
| Phosphoric acid | q.s. ad pH 1.5 |
| Tetrasodium EDTA | 0.05 |
| Light mineral oil | 3.0 |
| Hydrogen peroxide | 3.0 |
| Water | ad 100.0 |

The concentration of caffeine as compound according to b) may also be adjusted to 0.05%, 0.1%, or 0.5% or any values in between to achieve the same technical effect.

The concentration of hydrogen peroxide may be adjusted to 1%, 9%, 12%, 15%, or 20% by weight, or any value in between.

Example 3

Composition B

|  | % by weight |
| --- | --- |
| Theobromine | 0.01 |
| Cetearyl alcohol | 4.0 |
| Sodium lauryl sulfate | 1.5 |
| Phosphoric acid | q.s. ad pH 2.5 |
| Tetrasodium EDTA | 0.05 |
| Sunflower oil | 3.0 |
| Stearyl alcohol | 3.0 |
| Hydrogen peroxide | 6.0 |
| Water | ad 100.0 |

The concentration of theobromine as compound according to b) may also be adjusted to 0.05%, 0.1%, or 0.5% or any values in between to achieve the same technical effect.

Theobromine may also be replaced by xanthin or theophylline.

The concentration of hydrogen peroxide may be adjusted to 3%, 9%, 12%, 15%, or 20% by weight, or any value in between.

Example 4

Composition B

|  | % by weight |
| --- | --- |
| Caffeine | 0.01 |
| Theobromine | 0.05 |
| Theophylline | 0.05 |
| Cetearyl alcohol | 4.0 |
| Sodium lauryl sulfate | 0.8 |
| Phosphoric acid | q.s. ad pH 3.0 |
| Tetrasodium EDTA | 0.05 |
| Isopropyl myristate | 3.0 |
| Dimethicone 100 cs | 0.5 |
| Hydrogen peroxide | 3.0 |
| Water | ad 100.0 |

The concentration of theobromine as compound according to b) may also be adjusted to 0.05%, 0.1%, or 0.5% or any values in between to achieve the same technical effect.

Theobromine may also be replaced by xanthin or theophylline.

The concentration of hydrogen peroxide may be adjusted to 1%, 3%, 9%, 12%, 15%, or 20% by weight, or any value in between.

The invention claimed is:
1. A two-part oxidative dyeing composition, comprising:
a dyeing composition A having a pH in the range of 7 to 12, comprising:
one or more oxidative dye precursors and/or oxidative dye couplers, and
one or more alkalizing agents, and an aqueous oxidizing composition B having a pH in the range of 1 to 6, comprising:
  a) hydrogen peroxide
  b) one or more compounds according to the following structure:

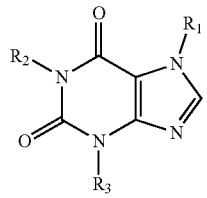

wherein $R_1$, $R_2$, and $R_3$ are independently selected from H and $CH_3$, and/or their mixtures, and
  c) one or more lipophilic compounds,
wherein composition B is an oil-in-water emulsion.

2. The composition according to claim 1, wherein the composition A comprises one or more oxidative dye precursors and/or oxidative dye couplers at a total concentration in the range of 0.001% to 10% by weight, calculated to the total weight of composition A.

3. The composition according to claim 1, wherein the composition A comprises one or more alkalizing agents selected from the group consisting of ammonia, a salt of ammonia, and an alkyl- or alkanolamine according to the general structure

wherein $R_4$, $R_5$, and $R_6$ are selected from H, from a $C_1$ to $C_4$ alkyl, a $C_3$ to $C_4$ unsaturated alkyl, a $C_3$ to $C_4$ branched alkyl, a $C_1$ to $C_4$ hydroxyl alkyl, a $C_3$ to $C_4$ unsaturated hydroxyl alkyl, and a $C_3$ to $C_4$ branched hydroxyl alkyl, with the condition that at least one of $R_4$, $R_5$, or $R_6$ is different from H.

4. The composition according to claim 1, wherein the alkalizing agent is at least one selected from the group consisting of ammonia, a salt of ammonia, monoethanolamine, 2-aminomethyl propanol, and a mixture thereof.

5. The composition according to claim 1, wherein the total concentration of alkalizing agents in the composition A is in the range of 0.25% to 15% by weight, calculated to the total weight of the composition A.

6. The composition according to claim 1, wherein the concentration of hydrogen peroxide in the composition B is in the range of 1% to 20% by weight, calculated to the total weight of the composition B.

7. The composition according to claim 1, wherein at least one compound according to b) is caffeine.

8. The composition according to claim 1, wherein the total concentration of the one or more compounds according to b) in composition B is in the range of 0.001% to 0.5% by weight, calculated to the total weight of the composition B.

9. The composition according to claim 1, wherein the one or more compounds according to c) is at least one selected from the group consisting of a $C_{12}$ to $C_{22}$ fatty alcohol, an ester of a $C_3$ to $C_{12}$ alcohols with a $C_{12}$ to $C_{22}$ fatty acid, a $C_8$ to $C_{22}$ fatty acid, a vegetable oil, a silicone, a hydrocarbon-based product, and a mixture thereof.

10. The composition according to claim 1, wherein the concentration of the one or more compounds according to c) is in the range of 1% to 20% by weight, calculated to the total weight of the composition B.

11. The composition according to claim 1, wherein at least one of the composition A and the composition B comprises one or more surfactants.

12. The composition according to claim 1, wherein at least one of the composition A and the composition B comprises one or more surfactants selected from the group consisting of a non-ionic surfactant, an anionic surfactant, a cationic surfactant, an amphoteric/zwitterionic surfactant, and a mixture thereof.

13. The composition according to claim 1, wherein at least one of composition A and composition B comprises one or more thickening polymers selected from the group consisting of an anionic thickening polymer, a non-ionic thickening polymer, and a cationic thickening polymer.

14. The composition according to claim 1, wherein the viscosity of composition B is in the range of 1,000 Pas to 25,000 mPas, determined by cone plate viscometry at 25° C. under atmospheric conditions.

15. A method for oxidative dyeing of keratin fibers, the method comprising:
  i) providing the two-part oxidative dyeing composition of claim 1 and mixing the compositions to provide a ready-to-use composition having a pH in the range of 7 to 12,
  ii) applying the ready-to-use composition onto keratin fibers and leaving the applied ready-to-use composition for a time period in the range of 1 to 60 min, and
  iii) rinsing off the keratin fibers and optionally shampooing the keratin fibers.

16. A kit-of-parts, comprising:
the two-part oxidative dyeing composition of claim 1 and a composition selected from:
  a bleach powder composition comprising at least one selected from the group consisting of a persalt, a peroxy salt, and an alkalizing agent; and
  an aqueous bleaching composition comprising one or more alkalizing agents and having a pH in the range of 7 to 12.

* * * * *